US012612616B2

(12) United States Patent
Chu et al.

(10) Patent No.: US 12,612,616 B2
(45) Date of Patent: Apr. 28, 2026

(54) SAMPLE PREPARATION APPARATUS AND MULTI-WELL PLATE WITH PCR CHIP

(71) Applicant: Siemens Healthcare Diagnostics Inc., Tarrytown, NY (US)

(72) Inventors: Daniel Chu, Hercules, CA (US); Alex Hofai Lee, Fremont, CA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 1075 days.

(21) Appl. No.: 17/640,686

(22) PCT Filed: Aug. 18, 2020

(86) PCT No.: PCT/US2020/070425
§ 371 (c)(1),
(2) Date: Mar. 4, 2022

(87) PCT Pub. No.: WO2021/056005
PCT Pub. Date: Mar. 25, 2021

(65) Prior Publication Data
US 2022/0325272 A1     Oct. 13, 2022

Related U.S. Application Data

(60) Provisional application No. 62/903,064, filed on Sep. 20, 2019.

(51) Int. Cl.
*C12Q 1/686*        (2018.01)
*C12N 15/10*        (2006.01)

(52) U.S. Cl.
CPC ......... *C12N 15/1013* (2013.01); *C12Q 1/686* (2013.01)

(58) Field of Classification Search
CPC ............ C12N 15/1003; C12N 15/1013; B01L 2300/0829
See application file for complete search history.

(56) References Cited

U.S. PATENT DOCUMENTS 8,691,149 B2      4/2014  Fritchie et al.
11,485,967 B2 *  11/2022  Anderson ........... C12N 15/1013
(Continued)

FOREIGN PATENT DOCUMENTS

CN          103789198        5/2014
CN          106916743        7/2017
(Continued)

OTHER PUBLICATIONS

International Search Report for PCT/2020/070425 dated Oct. 26, 2020.
(Continued)

*Primary Examiner* — Young J Kim

(57) ABSTRACT

An apparatus, multi-well plate and method for automated cell lysis and nucleic acid purification and amplification. The plate includes a lysis well, at least one wash well, an elution well, and a PCR chip. The apparatus includes a vertically aligned rotor mixer comprising a magnetic tip and actuators for moving the rotor mixer in a vertical and horizontal directions, to transfer magnetic beads from well to well. The rotor mixer is used to vortex lysis mixtures, wherein the vortexing speed is sufficient to overcome the magnetic attraction between the beads and mixer tip and disperse the beads in solution, to collect nucleic acids such as DNA in an elution solution that is transferred to the PCR chip for amplification of target sequences.

7 Claims, 15 Drawing Sheets

(56)  References Cited

U.S. PATENT DOCUMENTS

| | | |
|---|---|---|
| 2008/0227185 A1 | 9/2008 | Schonfeld et al. |
| 2012/0115738 A1 | 5/2012 | Zhou et al. |
| 2017/0218431 A1 | 8/2017 | Breidenthal et al. |
| 2018/0161769 A1 | 6/2018 | Kayyem et al. |

FOREIGN PATENT DOCUMENTS

| | | | | |
|---|---|---|---|---|
| EP | 3241901 | 11/2017 | | |
| KR | 102011496 | 8/2019 | | |
| WO | WO-9939010 A1 * | 8/1999 | .......... | C12Q 1/6806 |
| WO | 2011097424 | 8/2011 | | |
| WO | 2014071260 | 5/2014 | | |
| WO | WO-2014077400 A1 * | 5/2014 | ......... | G01N 21/6452 |

OTHER PUBLICATIONS

Qiagen:; "Qiagen one step RT-PCR kit"; technical product sheet; URL: ,www.qiagen.com/us/products/top-sellers/qiagen-onestep-rt-pcr-kiV#orderinginformation; 2013-2020.

Cao, Qingqing et al:; "Microfluidic Chip for Molecular Amplification of Influenza A RNA in Human Respiratory Specimens"; PLoS One; vol. 7, No. 3; DOI:10.1371/journal.pone.0033176 / Mar. 22, 2012.

\* cited by examiner

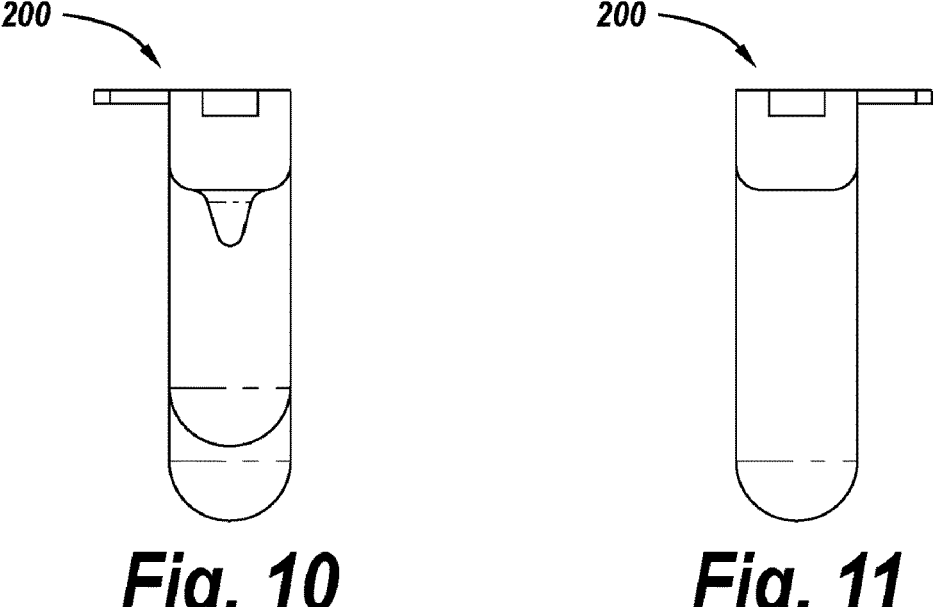
Fig. 10 Fig. 11
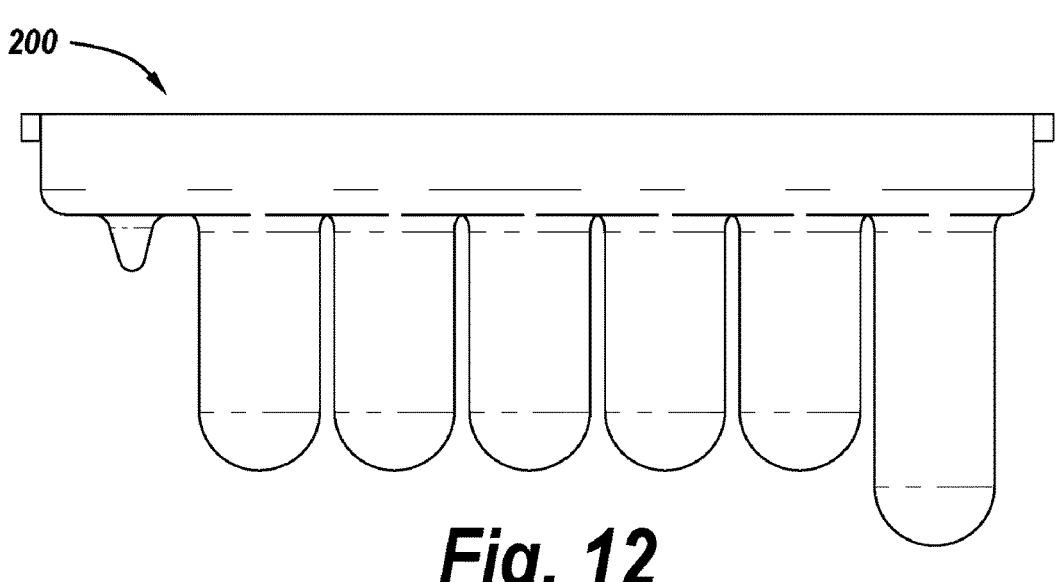
Fig. 12
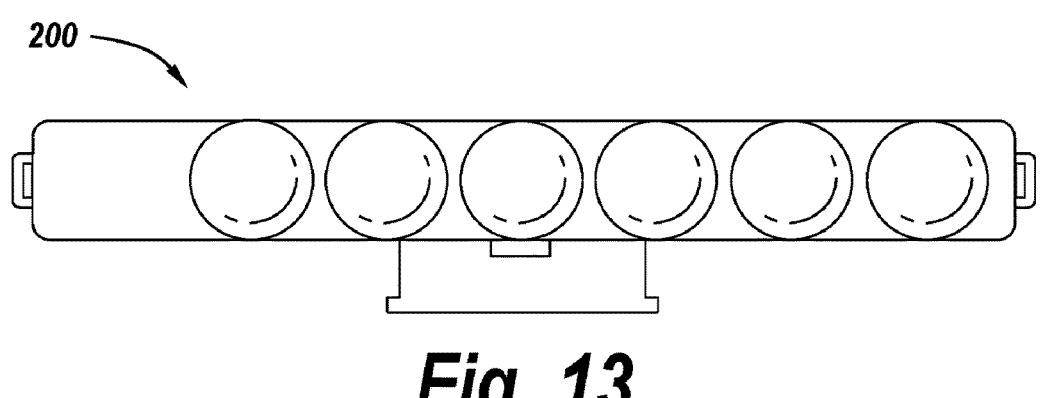
Fig. 13

Provide multi-well plate — 600

Load buffers in wells — 602

Introduce magnetic beads — 604

Introduce biological sample — 606

Vortex lysis mixture — 608

Apply external magnetic field to lysis well — 610

Wash beads — 612

Elute nucleic acids — 614

Apply external magnetic field to elution well — 616

Transfer eluted sample to PCR chip — 618

Amplify target DNA sequence — 620

Fluorometrically monitor product formation — 622

SAMPLE PREPARATION APPARATUS AND MULTI-WELL PLATE WITH PCR CHIP

CROSS-REFERENCE TO RELATED APPLICATIONS

N/A

FIELD OF THE DISCLOSURE

The disclosure herein relates generally to the field of cell lysing and nucleic acid purification and isolation. More particularly, the present disclosure relates to a novel rotor mixer and multi-well tray having particular utility in the field of nucleic acid extraction in molecular diagnostics.

BACKGROUND

In a typical cell lysis and nucleic acid isolation protocol using magnetic beads, a sample is moved by a pipette system to a well within a multi-well plate along with a cell lysis buffer and by a quantity of magnetic beads. The beads are functionalized, for example with silica surfaces, to allow selective binding of nucleic acid molecules such as DNA. A succession of mixing by external vibration, magnetic bead separation, supernatant aspiration, and dilution/washing steps are repeated with respect to the well. Heating of one or more of the wells of the multi-well plate may also be employed to facilitate lysis and/or binding. The sample transfer, washing, and elution steps require separate aspiration and dispensing tips to avoid cross-contamination.

Due to the common platform for processing multiple samples, heating and time of heating is limited and not customizable. A single overhead pipetting system is typically responsible for processing all samples within the multi-well plate.

An alternative system and technique involves the use of a magnet disposed within a sealed probe. The probe is selectively disposed within a respective well to allow the magnetic beads to be attracted to the probe by the magnet located within. In one embodiment, the probe may be removed from one well and inserted into fluid within another well. The magnet may then be extracted from within the probe, thus releasing the magnetic beads to be released from the probe surface. Further processing may then follow.

In the field of molecular diagnostics, there is a need for an efficient and cost-effective system and method for lysing cells and purifying samples for amplicon detection.

SUMMARY

In order to overcome the inflexibility and expense of the prior art automated processes for cell lysis and purification, the present disclosure provides a new rotor mixer featuring a magnetic tip. The rotor generates a vortex for combining a biological sample with a lysis buffer and magnetic beads, to form a lysis mixture in a lysis well. To optimize nucleic acid absorption on the magnetic beads, the vortexing speed is sufficient to overcome the magnetic attraction between the beads and the magnetic tip of the rotor mixer and allow the beads to disperse freely in the lysis mixture. When vortexing stops, the beads reattach to the magnetic tip. As a result, the rotor tip can be used to transfer the beads from the lysis mixture to and between other wells where they undergo washing and finally elution of the nucleic acids collected from the sample lysate.

As compared to traditional laboratory vortexing equipment using external vibration of sample wells, the rotor mixer with a magnetic tip provides an efficient, easy and reliable means for transferring magnetic beads between wells, and this setup is particularly suitable to automated sample preparation techniques.

Also provided for use with the rotor mixer is a disposable multi-well plate having a series of open fluid wells. A first well serves as lysis vessel where the lysis mixture is processed by rotor-induced vortexing and the magnetic beads bind to nucleic acid molecules. Other wells serve as washing vessels where the beads are treated with wash buffer to remove undesired lysis mixture residue. In a last, elution well, the washed beads are immersed in elution buffer to collect the nucleic acid molecules from the original sample lysate. Provision is also made for selective, customizable direct heating of one or more of the lysis well and elution well to enhance lysing and/or elution, if desired.

The present system and method enable the provision of multi-well plates with wells preloaded with buffers by the manufacturer, thereby speeding up the overall process and diminishing the likelihood of operator error. Alternatively, multiple trays may be provided in bulk, in a stacked configuration, optionally with each lysis well having respective preloaded magnetic beads.

Other unique features of the presently disclosed system and method include the provision of a disposable protective sleeve to protect the magnetic tip of the rotor during vortexing and other steps of nucleic acid isolation processes. Optionally, the protective sleeve may be fitted by vortex-increasing features such as propeller-shaped projections or paddles.

BRIEF DESCRIPTION OF THE DRAWINGS

Illustrative embodiments of the disclosed technology are described in detail below with reference to the attached drawing figures, which are incorporated by reference herein and wherein:

FIG. 10 is a rear view of the of the multi-well plate of FIG. 7;

FIG. 11 is front view of the multi-well plate of FIG. 7;

FIG. 12 is a side view of the multi-well plate of FIG. 7;

FIG. 13 is a bottom view of the multi-well plate of FIG. 7; and

DETAILED DESCRIPTION

Disclosed herein is an apparatus for extracting nucleic acids such as DNA molecules from biological samples. Use of the presently disclosed and described apparatus enables simplified, easy, and reliable transfer of magnetic beads between wells in a fashion particularly suitable to automated sample preparation techniques.

Figure 1:
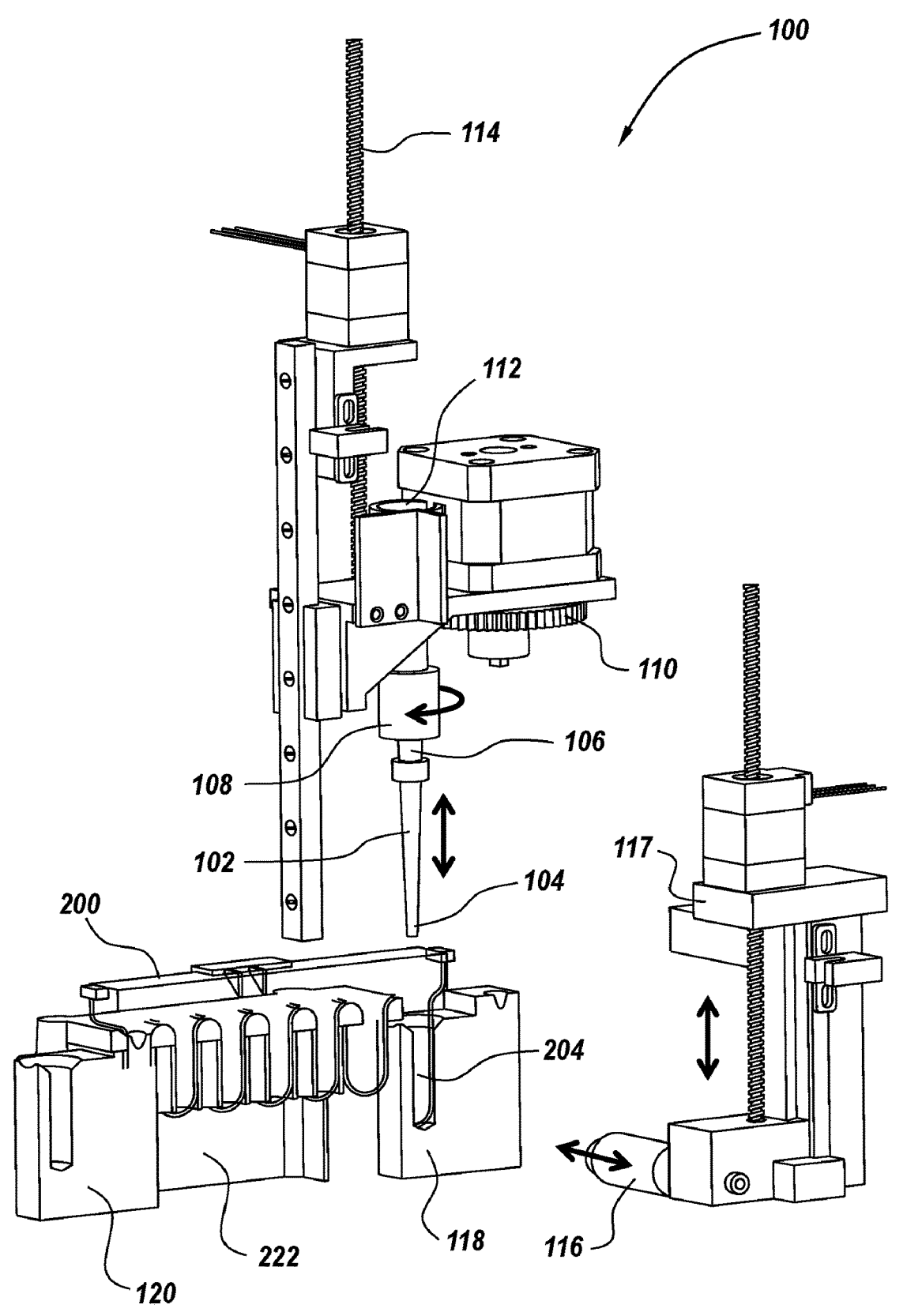
FIG. 1 is a perspective view of a sample lysis and nucleic acid extraction apparatus according to the present disclosure.

FIG. 1 illustrates an exemplary embodiment of an apparatus 100 according to the present disclosure. The apparatus 100 is comprised of a rotor mixer 102 having a magnetic tip 104, such as a ferromagnetic material enclosed within an inert polymeric coating, connected to rotor hub 108 via rotor shaft 106. A disposable protective sleeve, in this instance conically-shaped transparent plastic sleeve 107 shown in FIG. 2, protects magnetic tip 104 and rotor shaft 106 from the contents of buffers and mixtures that are used in nucleic acid extraction. Rotor engine 110 powers rotor mixer 102 when vortexing mixtures of fluids and other components such as magnetic beads. When the rotor mixer 102 is not vortexing, the beads magnetically attach to magnetic tip 104. Hence, when one of the steps of a nucleic acid isolation process is completed, the beads attached to the magnetic tip 104 can be easily transferred to another vessel where the next step is carried out. To this end, the apparatus is fitted with a vertical actuator 112 configured to move rotor mixer 102 in an upwardly or downwardly direction along vertical rail 114 and with a horizontal actuator (not shown) for repositioning the rotor mixer 102 from a vessel to another. In addition, the apparatus 100 may include an external magnet 116 that may be selectively translated to and away from a side wall of a vessel in order to attract and release, respectively, magnetic beads disposed within a vessel. The external magnet may also be selectively, vertically translated relative to the vessel, as will be discussed subsequently.

The vessels may be provided in the form of process wells in a disposable multi-well plate or holder for use in cell lysing and nucleotide purification. Use of the presently disclosed and described multi-well plate enables simplified and faster cell lysis and nucleotide extraction as compared to currently practiced methods. FIGS. 7-13 illustrate an embodiment of a multi-well plate 200 having a body member and a plurality of wells extending in a downwardly direction from the floor of the body member, according to the present disclosure. In this embodiment, the body member is a channel 202 and the process wells include a lysis well 204, wash wells 206, 208, 210, 212, 214, and elution well 216. The channel may help inhibit the unintended flow of working fluid off the multi-well plate.

Lysis well 204 is disposed at a first end 201 of the multi-well plate while the wash wells are disposed intermediate the first end and an opposite second end 203 where elution well 216 is located. Each well extends in a substantially orthogonal direction from the floor of the channel 202 and has an interior volume communicating with the channel via an aperture in the channel floor. The illustrated apertures are circular and coplanar with the floor surface, although embodiments of differing shapes and orientations are also contemplated. The apertures are also substantially colinear along the floor surface and are centered about a longitudinal axis 218 of the multi-well plate.

In one embodiment, the wells of 100 are pre-filled with appropriate buffers and other components and then sealed off, for example with a peel-away layer that is removed at the time of use. In another embodiment, the wells each have a tapered lower extent. This enables multiple multi-well plates to be vertically stacked, whereby the outer surface of a lysis well of a first holder is received within the lysis well of a lower, second holder. Similarly, the outer surfaces of the wash wells of the first holder are each received within a respective wash well of the lower, second holder.

In order to optimize vortexing and bead collection performance, the lower extent of lysis well 204 may have a geometry capable of receiving the magnetic tip 104. As seen for example in the side section view of FIG. 8, lysis well 204 may have a larger volume than the wash wells in order to provide sufficient space for the biological sample, lysis buffer, and magnetic beads. Conversely, elution well 216 may have a smaller volume than the wash wells in order to minimize dilution of the final nucleic acid product and may be characterized by a conical cross-section to facilitate removal of the product with a pipettor or other devices for transferring fluids.

The lysis well 204 of the multi-well plate 200 may be subjected to heating, depending upon the characteristics of the lysis process implemented therewith. For example, the outer surface of the lower extent of the lysis well 204 may be configured to be received within a heater external to the unitary structure. Such a heater may be a heating block 118 placed beneath the holder, receiving the outer surface of the lower extent of the lysis well therewithin for a required or desired time period. Similarly, the elution well 216 of the multi-well plate 200 may be heated with another heater external to the unitary structure, such as heating block 120, depending upon the elution process implemented therewith.

The multi-well plate 200 may be provided with retention features, such as tab 220 projecting from the upper rim of channel 202 or other lateral projections extending from the multi-well plate on either side of the multi-well plate 200. During processes such as heating and vortexing, when external devices move relative to the multi-well plate 200, the retention features may be selectively engaged by external gripping mechanisms, thereby maintaining the multi-well plate in a fixed position relative to the external devices. The retention features may also be of use during the introduction of samples, buffers, beads or other components in the wells or eluted product retrieval as a pipetting system presses down on the inner surface of the elution well 216. Alternatively, the multi-well plate and associated heating blocks and support structures, i.e., the plate holder 222, may be configured for lateral, horizontal translation relative to the rotor mixer 102, thus obviating the need for enabling horizontal translation of the rotor mixer and associated components.

A non-limiting exemplary method of using the system of FIG. 1 in combination with the multi-well plate of FIGS. 7-13 is now described in conjunction with FIGS. 2-6 and 14. Not all steps need be practiced in the order described below, nor be utilized at all, depending upon the embodiment. First, in step 300, a multi-well plate such as described in the foregoing is provided and placed into plate holder 222. In step 302, one or more wash buffers are loaded into the wash wells, an elution buffer is loaded into elution well 216, and lysis buffer is loaded into the lysis well 204.

Magnetic beads 402 are also introduced in the lysis well 204, as at step 304. In one example, the material of the beads may be optimized for genomic DNA extraction from blood samples, but its composition may vary to suit other types of bodily fluids or tissues or for extracting other types of nucleic acids such as RNA. A biological sample is then loaded into the lysis well (step 306), yielding a lysis mixture ready for vortexing. Typical samples include blood, sputum, hair, and other bodily fluids and tissues, optionally pretreated for example by freezing, homogenizing, or grinding. Those of skill in the art will recognize that the choice of buffers and other reactants may vary according to the type of sample and beads to provide optimal conditions for nucleic acid extraction. While this illustrated process depicts a certain order of loading the lysis well to form the lysis mixture, other orders may be employed, such as disposing the sample into the lysis well prior to adding the magnetic beads.

Figure 2:
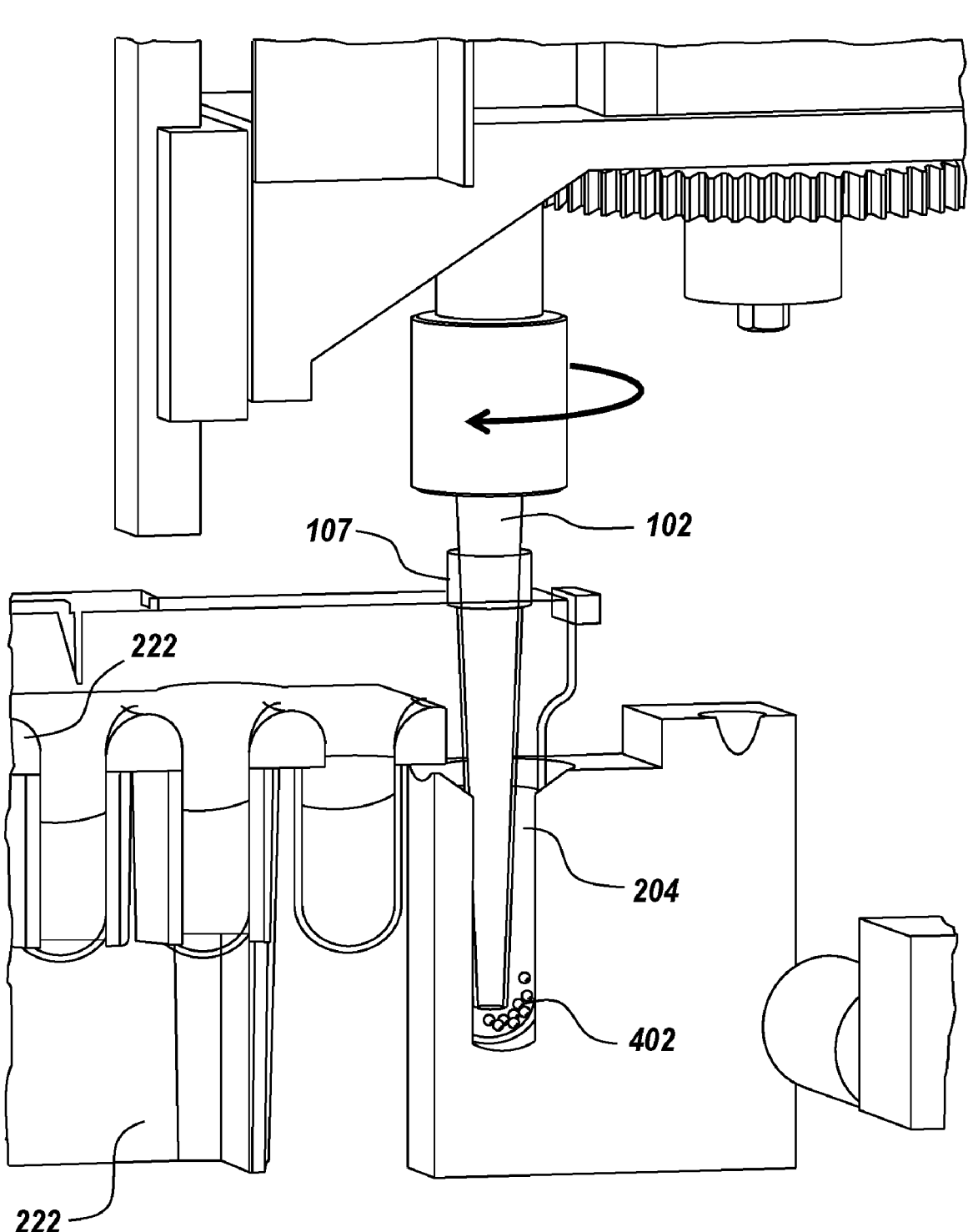
FIG. 2 illustrates vortexing of a lysis mixture by the apparatus of FIG. 1 in the presence of magnetic beads.

In step 308, the lysis mixture is vortexed by spinning the rotor mixer 102, as exemplified in FIG. 2, either continuously or intermittently. For at least a portion of the vortexing step, the rotor mixer 102 is spun at a rate sufficient to overcome attraction forces between magnetic beads 402 and magnetic tip 104, thereby freeing the beads to swirl about the lysis mixture and bind to nucleic acid molecules dispersed therein following cell lysis. In an exemplary embodiment, the rotor mixer spins at about 5,000 to about 10,000 revolutions per minute.

Figure 3:
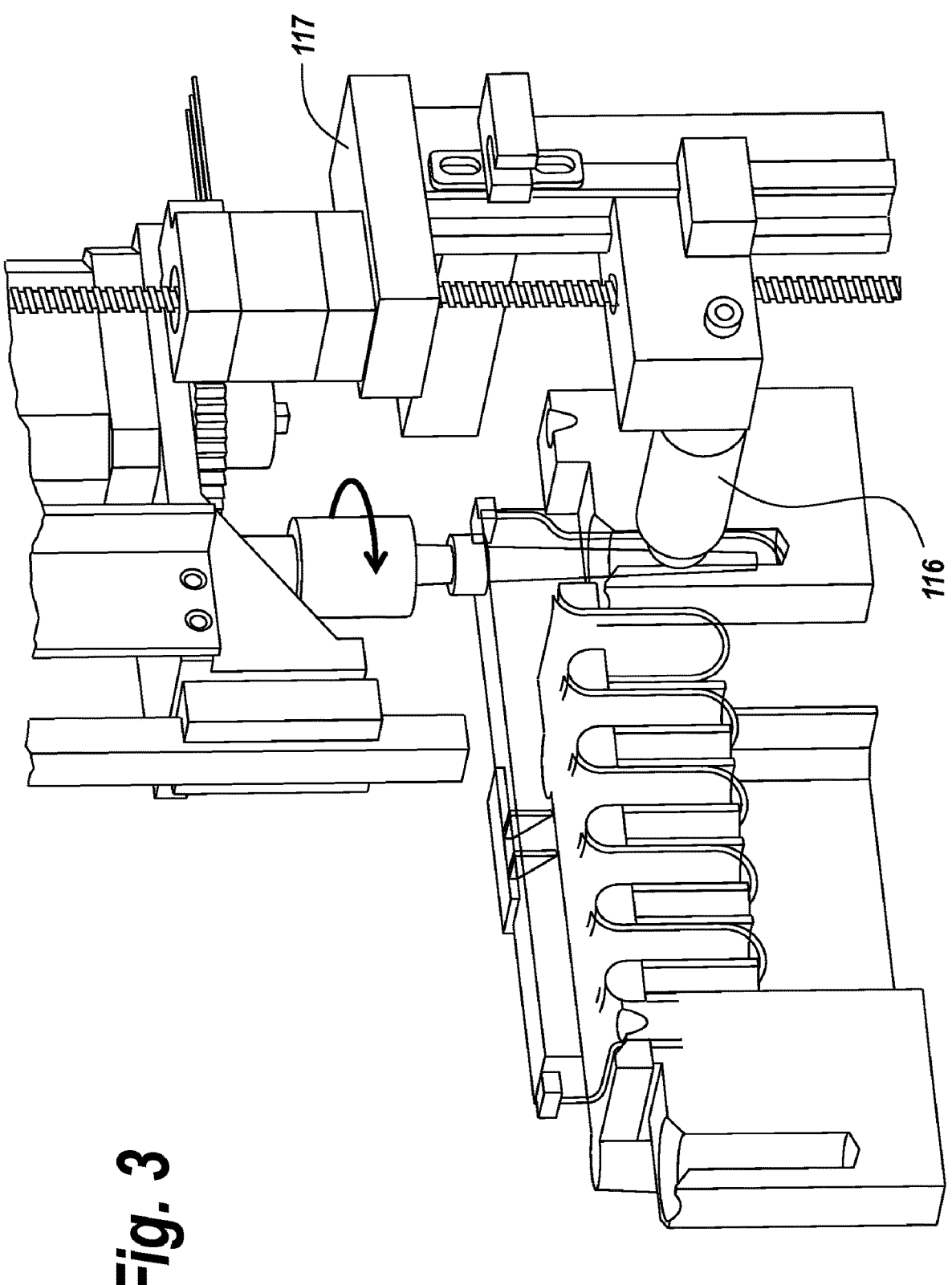
FIG. 3 illustrates the application of an external magnetic field to the lysis well of a multi-well plate.
Figure 4:
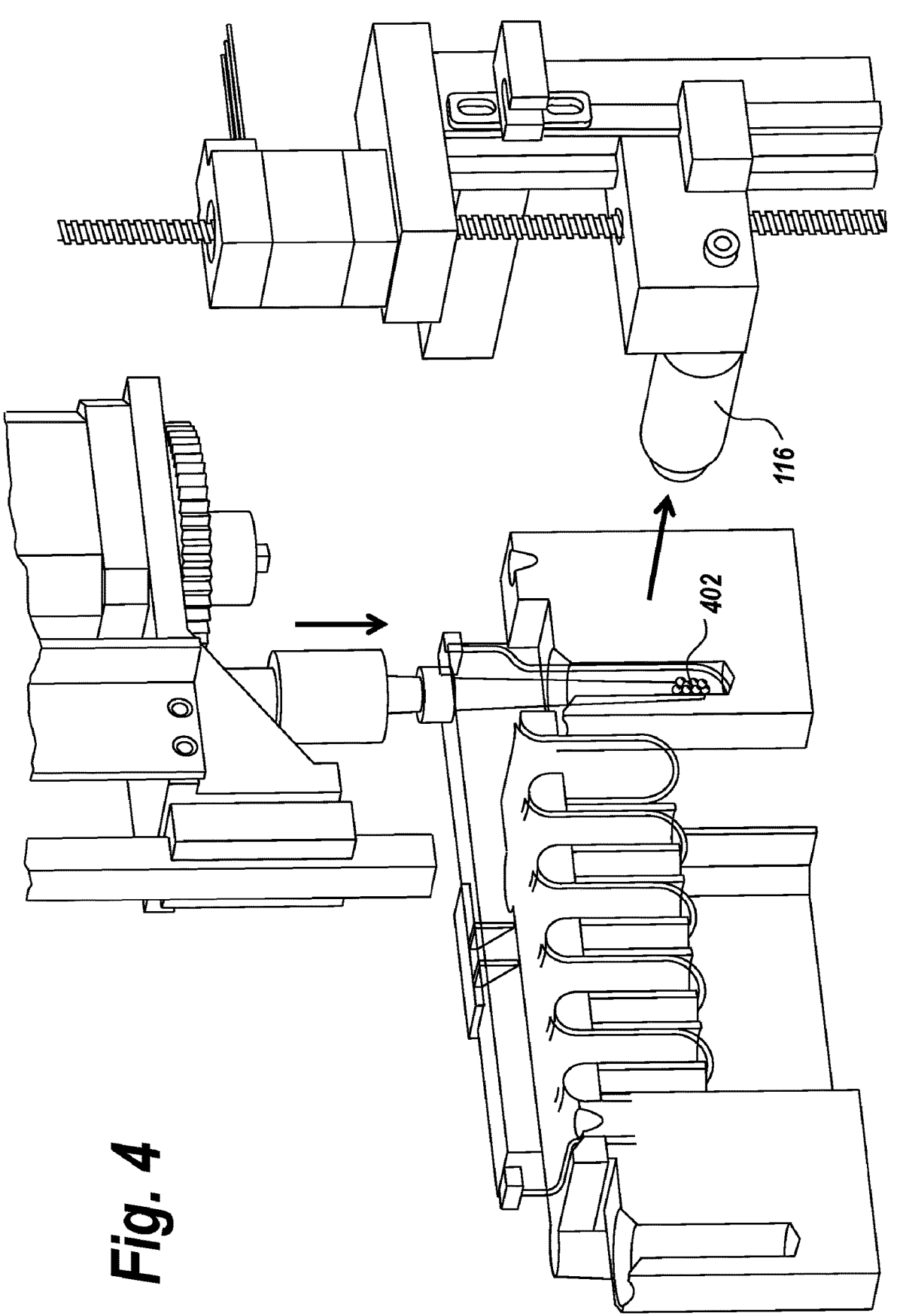
FIG. 4 illustrates removing the external magnetic field of FIG. 3 from the multi-well plate and lowering the magnetic tip, to collect the beads.

When vortexing ceases, magnetic beads 402 attach to magnetic tip 104. In instances where some or all the beads fail to attach and remain afloat or absorbed to the well wall, external magnet 116 may be translated to a side wall of lysis well 204 by operation of translation member 117 (FIG. 3). The rotor mixer 102 is temporarily moved upwards to a higher level of the lysis mixture, while the magnetic field exerted by external magnet 116 on the outer surface of the well forms the beads 402 into a cluster adhering to the well wall. External magnet 116, still pressed against the side of lysis well 204, is moved by the translation member first downwards, then away from well wall (FIG. 4), thereby removing its magnetic field and leaving the beads 402 resting at the bottom of well 204 and ready for collection (step 310). The rotor mixer is then lowered into the lysis well 204 whereby the beads 402 are gathered against the magnetic tip 104.

Figure 5:
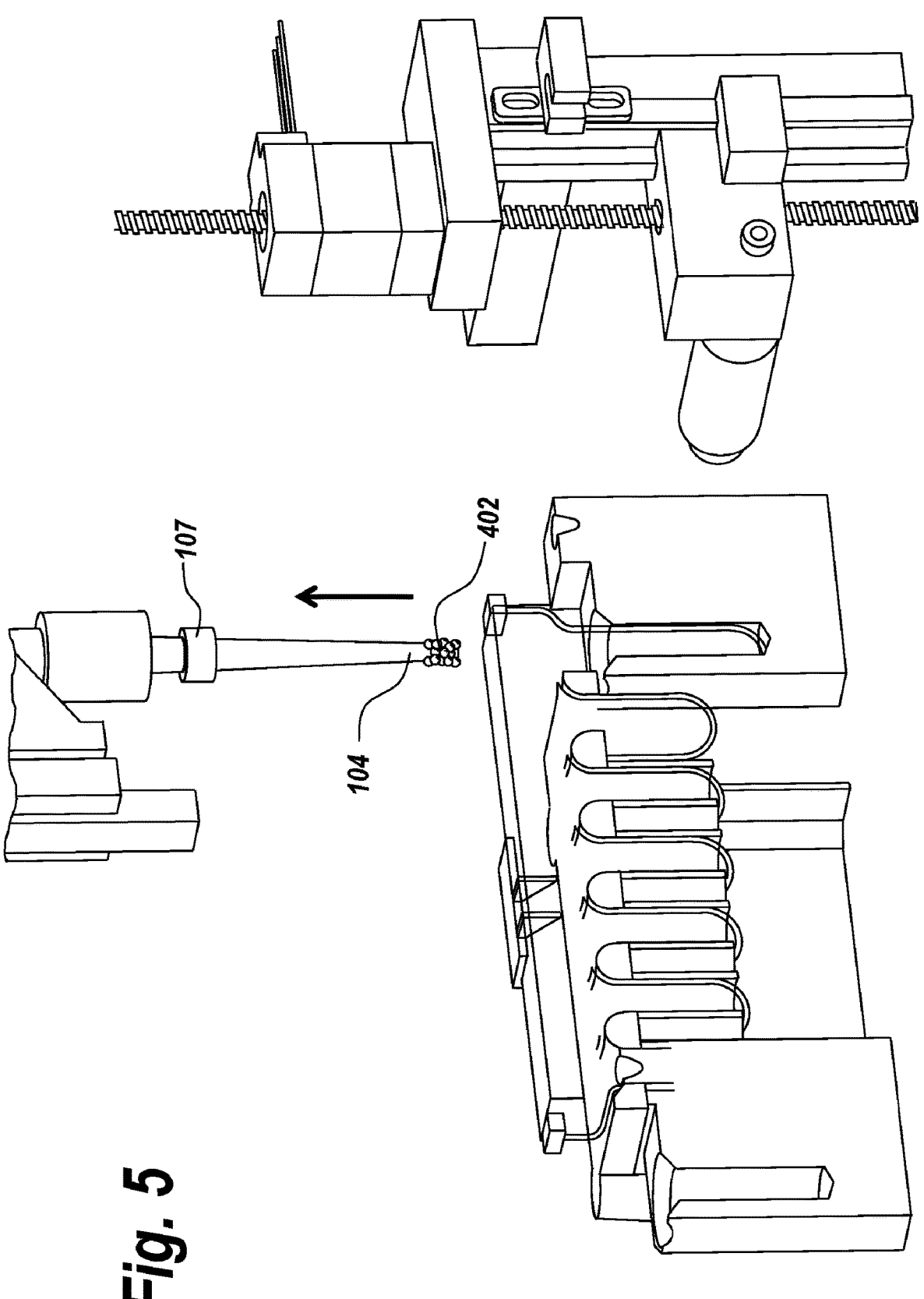
FIG. 5 illustrates removing the rotor mixer tip with the magnetic beads magnetically attached thereto from the lysis well.
Figure 6:
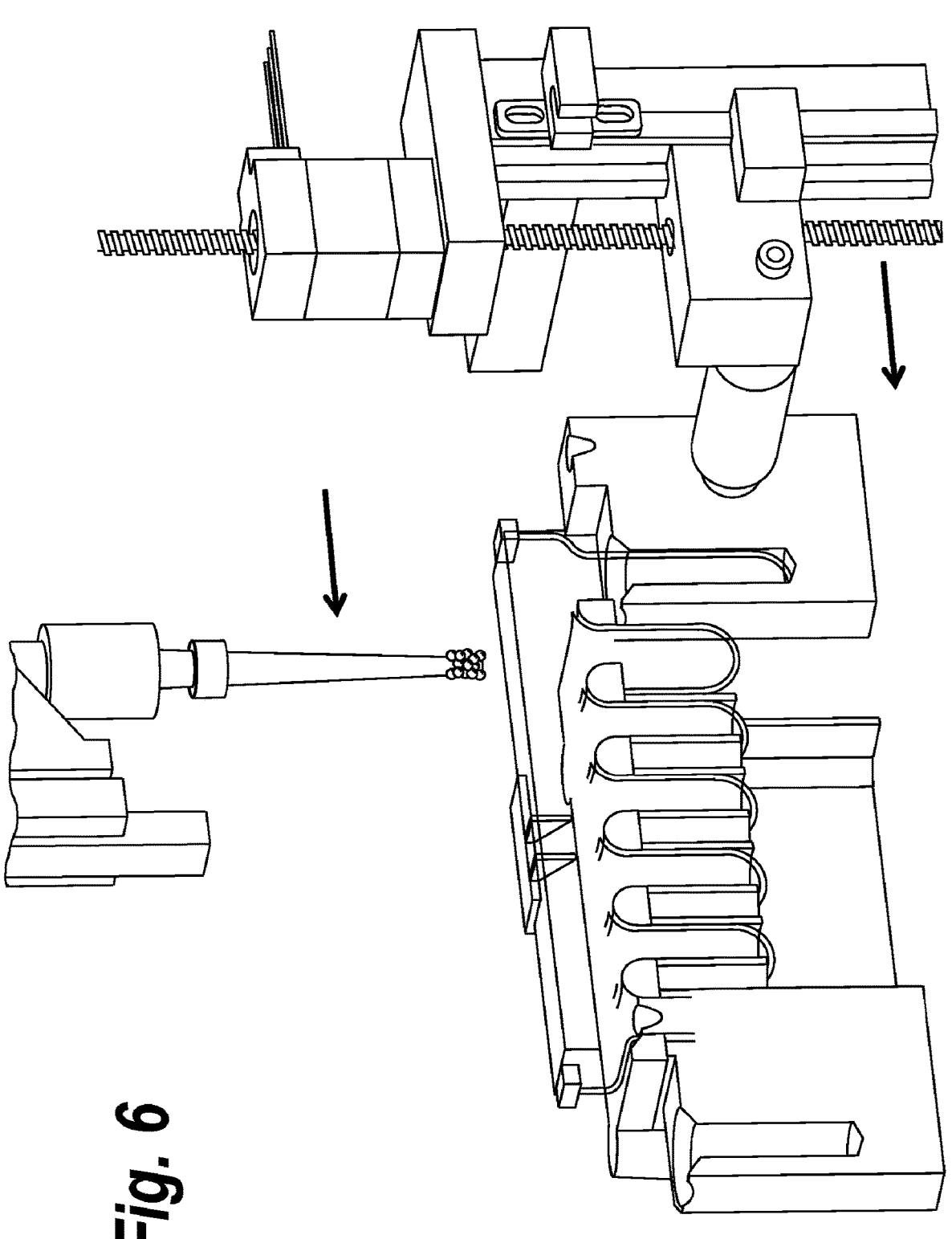
FIG. 6 illustrates horizontally moving the rotor mixer tip of the apparatus of FIG. 1 with the magnetic beads magnetically attached thereto towards a wash well.
Figures 7, 8, 9:
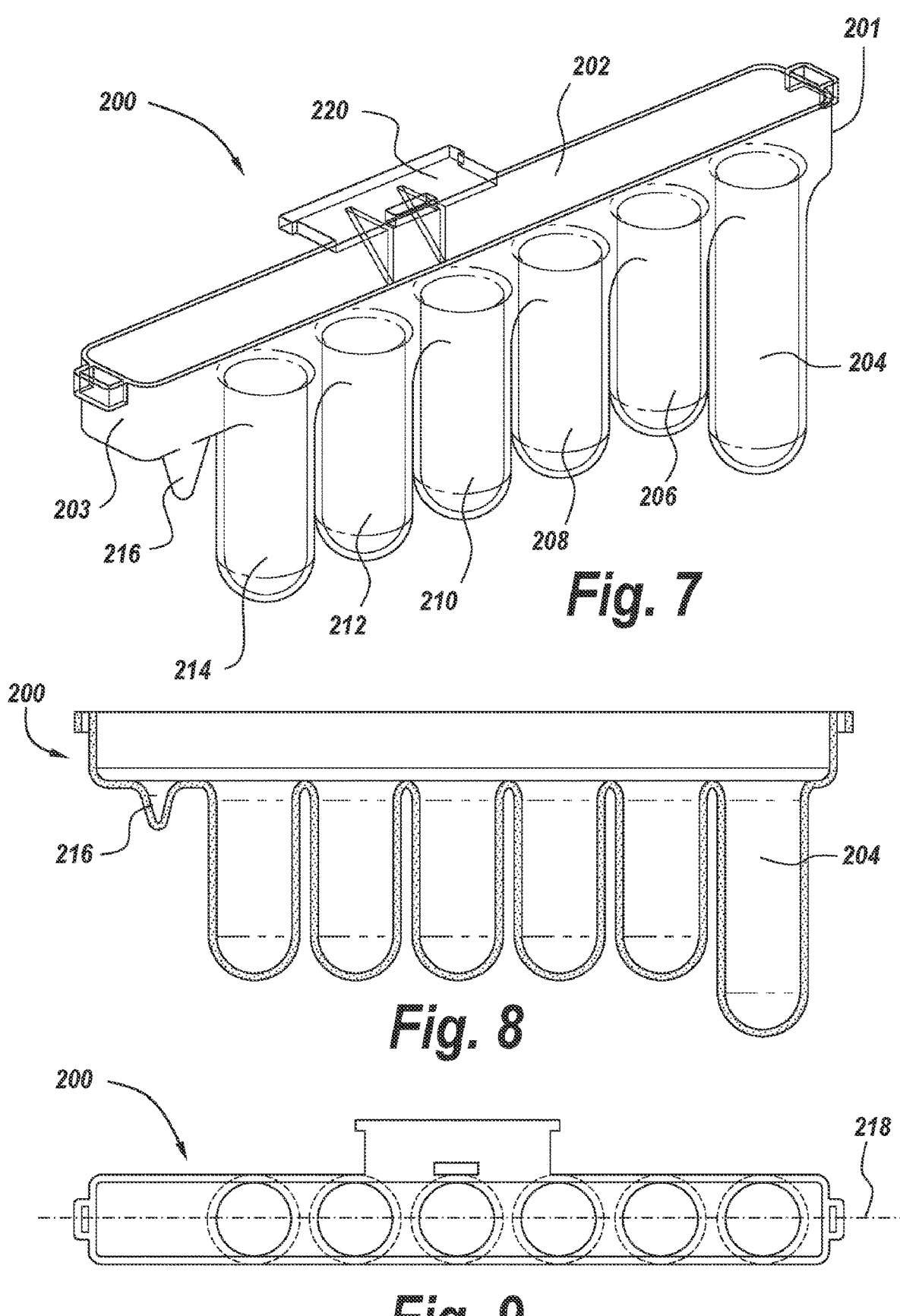
FIG. 7 is a perspective view of a multi-well plate according to the present disclosure.
FIG. 8 is a side section view of the multi-well plate of FIG. 7.
FIG. 9 is a top view of the multi-well plate of FIG. 7.
Figure 14:
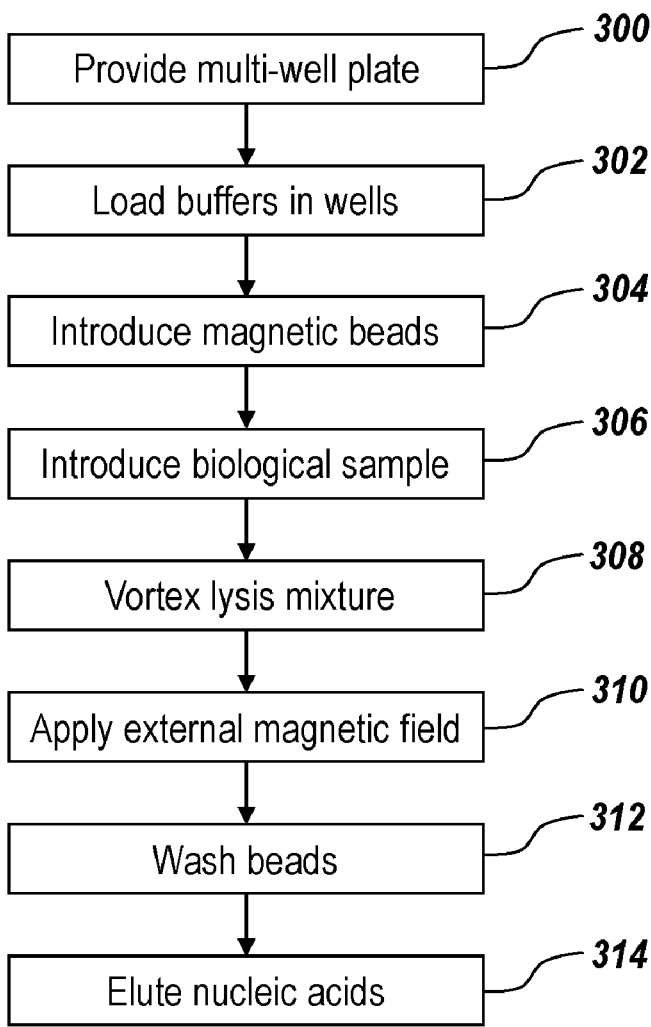
FIG. 14 is a flowchart of a method of nucleic acid sample lysis, purification, and elution.

In bead-washing step 312, vertical actuator 112 moves rotor mixer 102 in an upwardly direction, as illustrated in FIG. 5, thereby extracting tip 104 and the magnetic beads 402 attached thereto from lysis well 204. FIG. 6 shows the horizontal actuator (not shown) aligning rotor shaft 106 with one of wash wells, for example wash well 206. The external magnet 116 may also be moved horizontally in coordination with the rotor 102. Alternatively, the plate holder 222 may translate the multi-well plate 200 relative to the rotor and external magnet. Once properly aligned, the vertical actuator 112 moves the rotor mixer 102 in a downwardly direction, to immerse the magnetic tip 104 and the beads 402 attached thereto in a wash buffer contained in the wash well 206. A process similar to that executed within the lysis well 204 may then be carried out, including moving the external magnet 116 to a position adjacent the wash well, rotating the rotor to release the beads into the wash buffer and to allow the beads to gather on the wash well wall adjacent the external magnet, removing the external magnet, rotating the rotor again to resuspend the beads in the wash buffer, then ceasing rotation to allow the beads to reattach to the rotor magnetic tip 104. This process may also include vertically manipulating the external magnet to gather the beads in the bottom of the wash well prior to reintroducing the rotor and magnetic tip. This procedure can be repeated in any or all the other wash wells 208, 210, 212, and 214. After a desired number of washing steps have been completed, the vertical and horizontal actuators immerse magnetic tip 104 and magnetic beads 402 in elution well 216, where nucleic acids elute from magnetic beads 402 into the elution buffer (step 314).

As anticipated, the contents of the lysis well 204 may be heated prior to the illustrated step 310 of applying an external magnetic field to an exterior surface of the lysis well. Following removal of the beads 402, liquid residues in the lysis well and the wash wells may be aspirated by a pipetting system and dispensed to a waste receptacle. Similarly, elution well 216 may undergo heating at any point prior to removal of the final nucleotide product solution.

In a further aspect, DNA samples in elution well 216 may be directly transferred to a self-contained polymerase chain reaction (PCR) chip for in situ amplification and analysis. This approach allows for inexpensive and rapid point-of-care (POC) testing of infectious diseases and genomic profiling which can be automated and thereby require less operator supervision than traditional diagnostic laboratory procedures.

Figure 15:
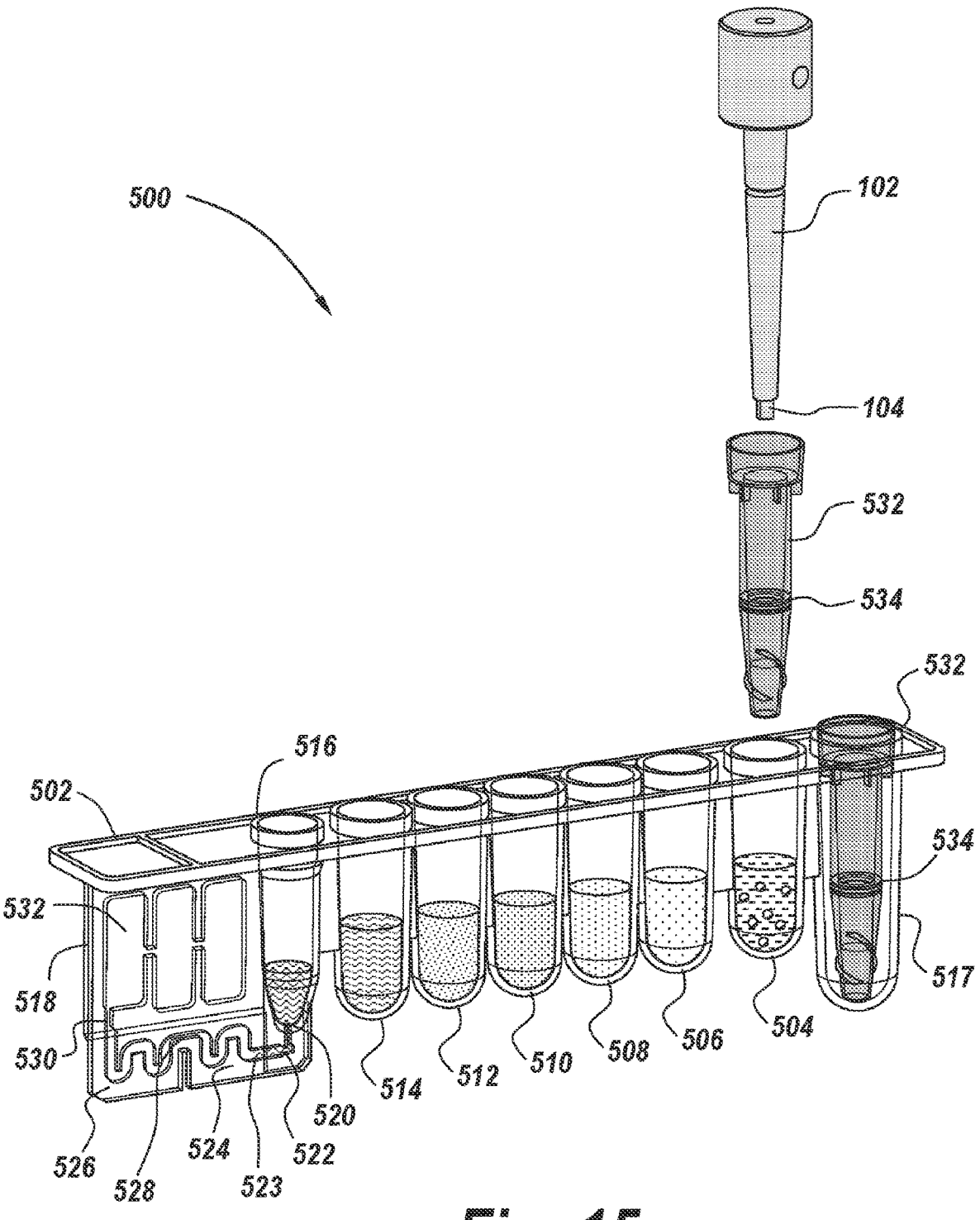
FIG. 15 is a perspective view of a multi-well plate fitted with a PCR chip according to the present disclosure.

For ease of operation, the PCR chip may be an integral part of the multi-well plate. FIG. 15 illustrates a multi-well plate 500 having a body member 502 extending from a first end to an opposite second end of the plate. In addition to lysis well 504, wash wells 506, 508, 510, 512, 514, and elution well 516, the plate includes PCR chip 518. In this instance, the PCR chip is formed of channels and chambers sealed with plastic film(s), but those of skill in the art will understand that any type of self-contained PCR chip whose geometry and relevant features are suitable with the other components of the setup may also serve the same purpose.

DNA sample delivery channel 522 connects aperture 520 at the bottom end of elution well 516 with the PCR chip. Specifically, channel 522 communicates with a first heat zone 524 which is in turn hydraulically connected to second heat zone 526. Each of the heat zones may be heated to the temperature of a given step of a PCR process, for example by means of PCR chip heating elements added to apparatus 100 (not shown). In one embodiment, the first heat zone is heated to temperatures associated with the PCR denaturing stage, typically between about 85° C. and about 95° C., while the second heat zone is heated to temperatures associated with the PCR annealing stage, typically between about 50° C. and about 60° C. Intermediate channel 528 connects the first heat zone and second heat zone, and, being at an intermediate position between the two, may be heated to temperatures associated with the PCR extension step, typically between 65° C. and 75° C. Channel 530 connects the second heat zone with expansion chamber 532.

In one embodiment, all the components required for PCR amplification of the DNA template to be assayed in the biological sample are included in the PCR chip. PCR components usually include Taq DNA polymerase enzyme, deoxynucleotide triphosphates (dNTPs), cofactors such as $MgCl_2$, and PCR primers specific to the DNA sequence that is the subject of the diagnostic procedure, e.g., genomic DNA of an infectious disease or patient DNA bearing oncogenic mutations. The PCR components may be provided as a solution or in the form of dry mixture 523, and their respective amounts are usually calibrated to optimize PCR yield following addition of the elution solution.

Multi-well plate also features sleeve storage well 517 where protective sleeves 532 are kept at the ready for use. The sleeve storage well may have a larger volume than the wash wells in order to provide sufficient space to accommodate a sleeve. The protective sleeve 532 includes O-ring seal 534 which enables pumping action by the sleeve when moved along its vertical axis, as illustrated below. In one embodiment, the wells of 500 are pre-filled with appropriate buffers and other components and then sealed off, for example with a peel-away layer that is removed at the time of use.

The multi-well plate 500 may be provided with retention features, such as tabs projecting from body member 502 or other lateral projections extending from the multi-well plate on either side of the multi-well plate 500. During processes such as heating, vortexing, and PCR, when external devices move relative to the multi-well plate 500, the retention features may be selectively engaged by external gripping mechanisms, thereby maintaining the multi-well plate in a fixed position relative to the external devices. The retention features may also be of use during the introduction of samples, buffers, beads or other components in the wells or eluted product pumping as the sleeve 532 presses down on the bottom end of the elution well 516. Alternatively, the multi-well plate and associated heating blocks and support structures, i.e., the plate holder 222, may be configured for lateral, horizontal translation relative to the rotor mixer 102, thus obviating the need for enabling horizontal translation of the rotor mixer and associated components.

A non-limiting exemplary method of using the system of FIG. 1 in combination with the multi-well plate of FIG. 15 is now described in conjunction with FIGS. 16-22. Not all steps need be practiced in the order described below, nor be utilized at all, depending upon the embodiment. First, in step 600, a multi-well plate such as described in the foregoing is provided and placed into plate holder 222. In step 602, one or more wash buffers are loaded into the wash wells, an elution buffer is loaded into elution well 516, and lysis buffer is loaded into the lysis well 504.

Magnetic beads 402 are also introduced in the lysis well 504, as at step 604. In one example, the material of the beads may be optimized for genomic DNA extraction from blood samples, but its composition may vary to suit other types of bodily fluids or tissues or for extracting other types of nucleic acids such as RNA. A biological sample is then loaded into the lysis well (step 606), yielding a lysis mixture ready for vortexing. Typical samples include blood, sputum, hair, and other bodily fluids and tissues, optionally pretreated for example by freezing, homogenizing, or grinding. Those of skill in the art will recognize that the choice of buffers and other reactants may vary according to the type of sample and beads to provide optimal conditions for nucleic acid extraction. While this illustrated process depicts a certain order of loading the lysis well to form the lysis mixture, other orders may be employed, such as disposing the sample into the lysis well prior to adding the magnetic beads.

Figure 16:
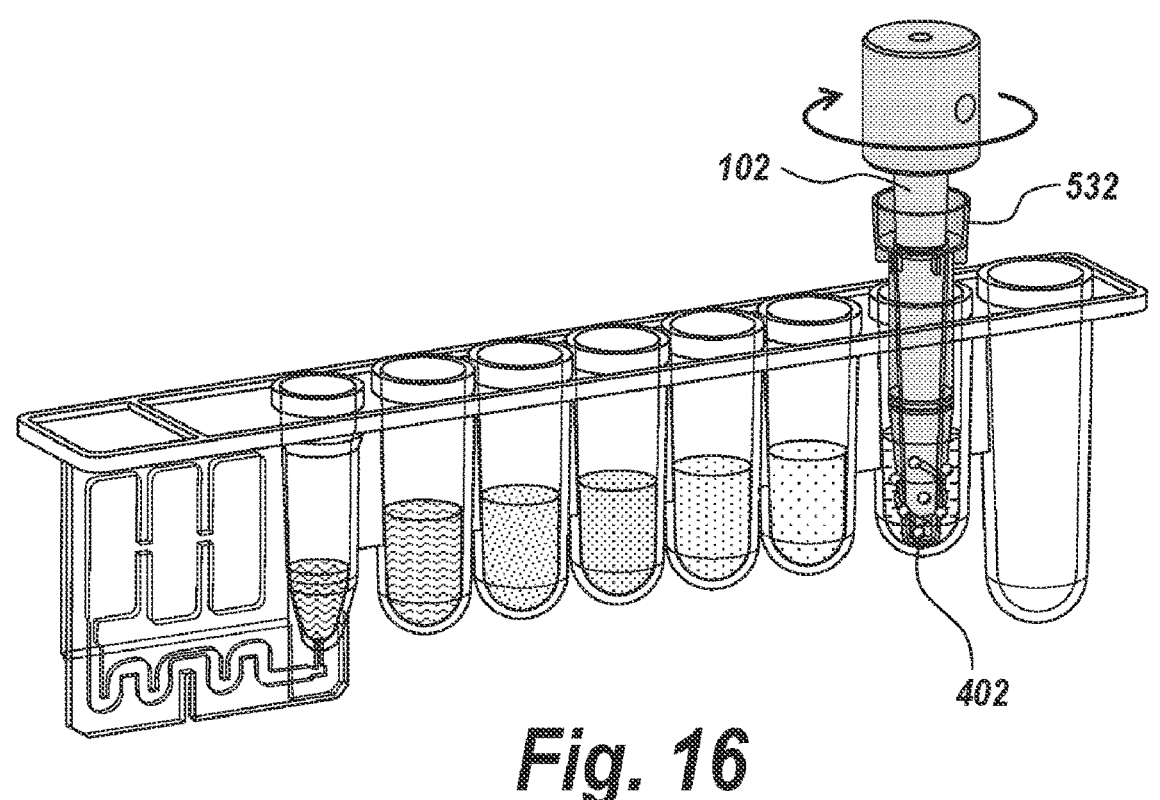
FIG. 16 illustrates vortexing of a lysis mixture by the apparatus of FIG. 1 in the presence of magnetic beads inside the lysis well of the multi-well plate of FIG. 15.

In step 608, the lysis mixture is vortexed by spinning the rotor mixer 102, as exemplified in FIG. 16, either continuously or intermittently. For at least a portion of the vortexing step, the rotor mixer 102 is spun at a rate sufficient to overcome attraction forces between magnetic beads 402 and magnetic tip 104, thereby freeing the beads to swirl about the lysis mixture and bind to nucleic acid molecules dispersed therein following cell lysis. In an exemplary embodiment, the rotor mixer spins at about 5,000 to about 10,000 revolutions per minute.

When vortexing ceases, magnetic beads 402 attach to magnetic tip 104. In instances where some or all the beads fail to attach and remain afloat or absorbed to the well wall, external magnet 116 may be translated to a side wall of lysis well 204 by operation of translation member 117 in a manner analogous to that described above in reference to FIG. 3. The rotor mixer 102 is temporarily moved upwards to a higher level of the lysis mixture, while the magnetic field exerted by external magnet 116 on the outer surface of the well forms the beads 402 into a cluster adhering to the well wall. In a manner analogous to that described above in reference to FIG. 4, external magnet 116, still pressed against the side of lysis well 504, is moved by the translation member first downwards, then away from well wall, thereby removing its magnetic field and leaving the beads 402 resting at the bottom of well 504 and ready for collection (step 610). The rotor mixer is then lowered into the lysis well 504 whereby the beads 402 are gathered against the magnetic tip 104.

Figure 17:
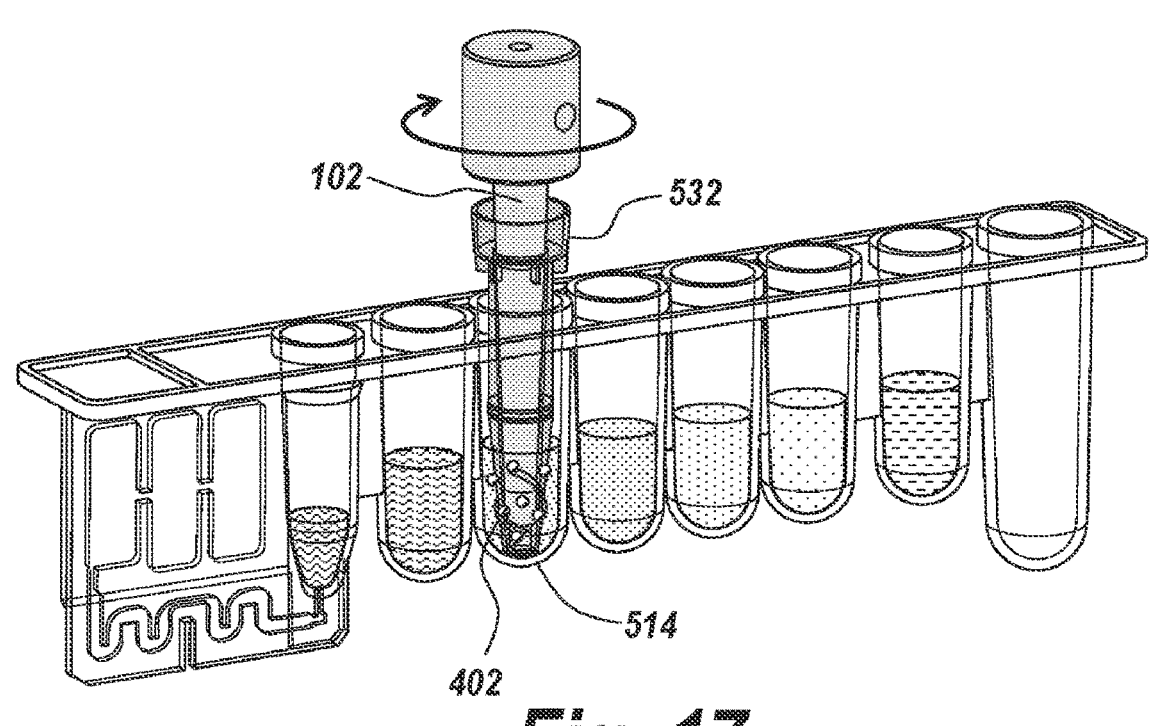
FIG. 17 illustrates washing the magnetic beads of FIG. 16 in a wash well of the multi-well plate of FIG. 15.

In bead-washing step 612, vertical actuator 112 moves rotor mixer 102 in an upwardly direction, thereby extracting tip 104 and the magnetic beads 402 attached thereto from lysis well 504. The horizontal actuator (not shown) then aligns rotor mixer 102 with one of the wash wells, for example wash well 514. The external magnet 116 may also be moved horizontally in coordination with the rotor mixer 102. Alternatively, the plate holder 222 may translate the multi-well plate 500 relative to the rotor mixer and external magnet. A process similar to that executed within the lysis well 504 may then be carried out, including moving the external magnet 116 to a position adjacent the wash well, rotating the rotor mixer to release the beads into the wash buffer and to allow the beads to gather on the wash well wall adjacent the external magnet, removing the external magnet, rotating the rotor again to resuspend the beads in the wash buffer, then ceasing rotation to allow the beads to reattach to the rotor magnetic tip 104 (FIG. 17). This process may also include vertically manipulating the external magnet to gather the beads in the bottom of the wash well prior to reintroducing the rotor and magnetic tip. This procedure can be repeated in any or all the other wash wells 506, 508, 510, and 512 in whichever order. After a desired number of washing steps have been completed, the vertical and horizontal actuators immerse magnetic tip 104 and magnetic beads 402 in elution well 516, where nucleic acids elute from magnetic beads 402 into the elution buffer (step 614).

As anticipated, the contents of the lysis well 204 may be heated prior to the illustrated step 610 of applying an external magnetic field to an exterior surface of the lysis well. Following removal of the beads 402, liquid residues in the lysis well and the wash wells may be aspirated by a pipetting system and dispensed to a waste receptacle. Similarly, elution well 516 may undergo heating at any point prior to pumping the eluted sample 536 to PCR chip 518.

Figure 18:
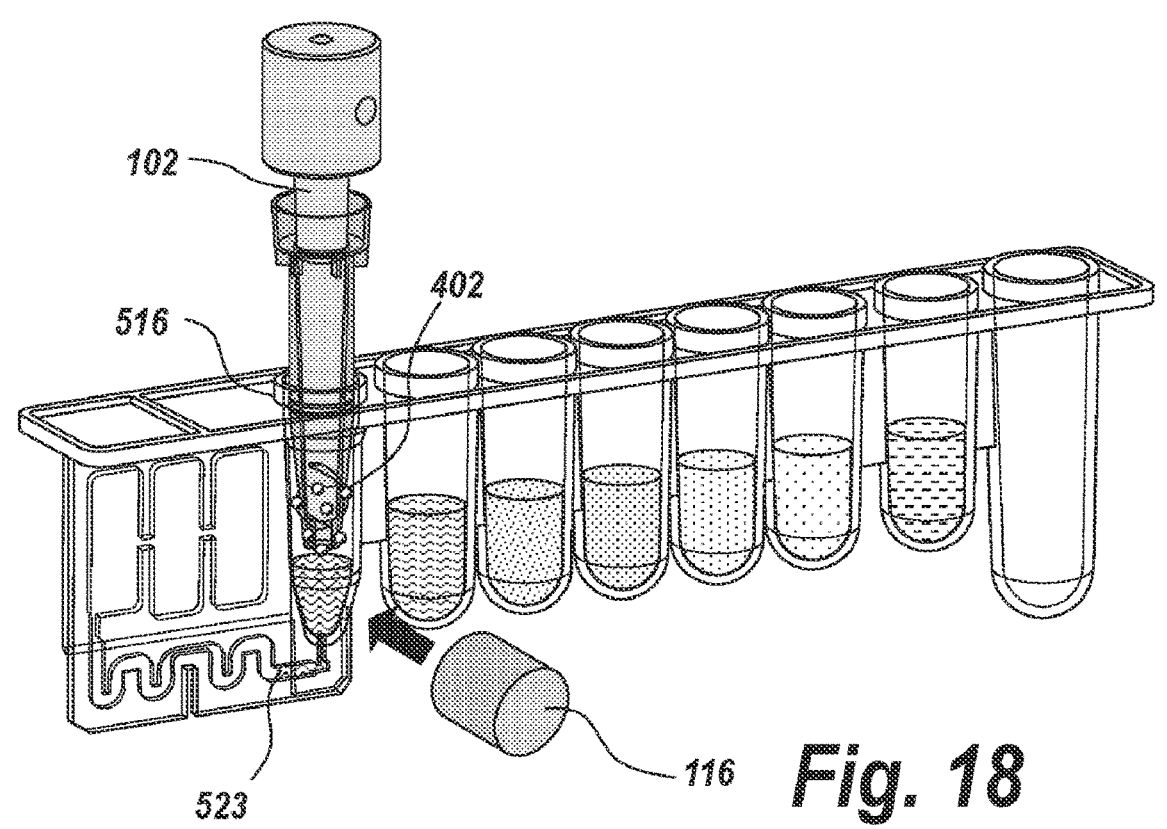
FIG. 18 illustrates applying an external magnetic field to the elution well of the multi-well plate of FIG. 15.
Figure 19:
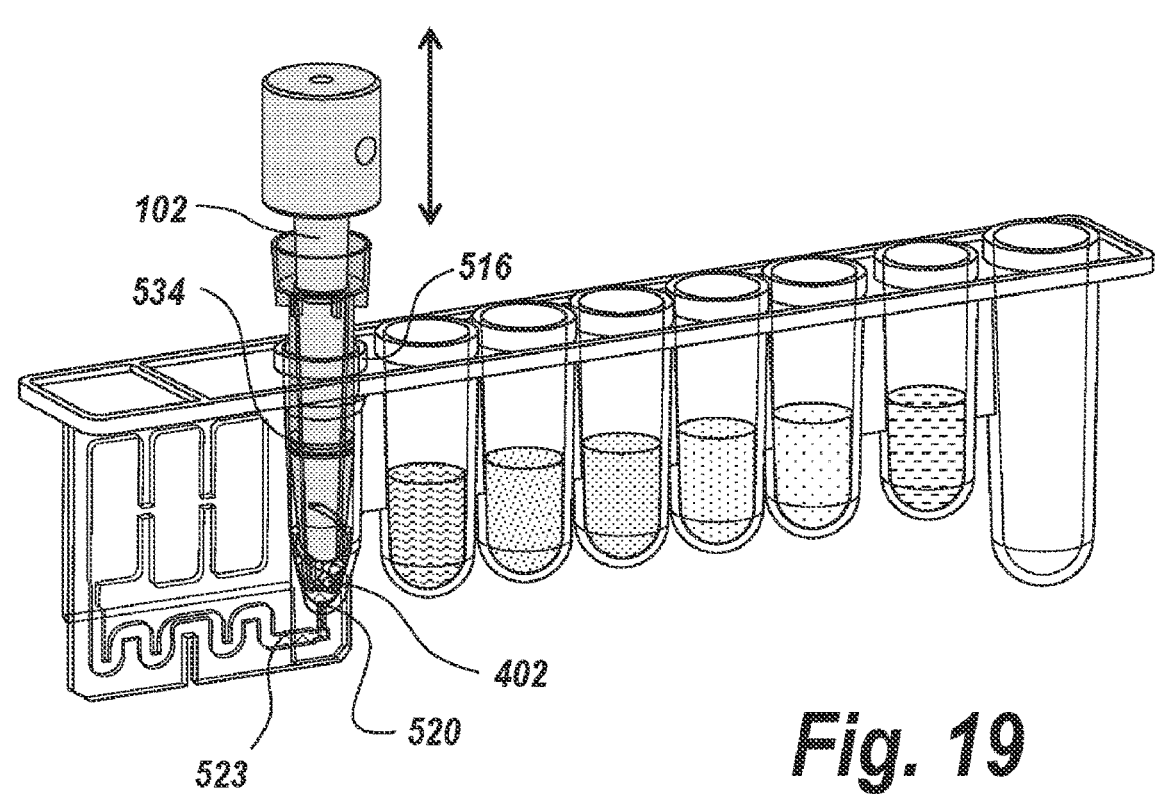
FIG. 19 illustrates the magnetic beads clustering on the side wall of the elution well under the action of the external magnetic field.
Figure 20:
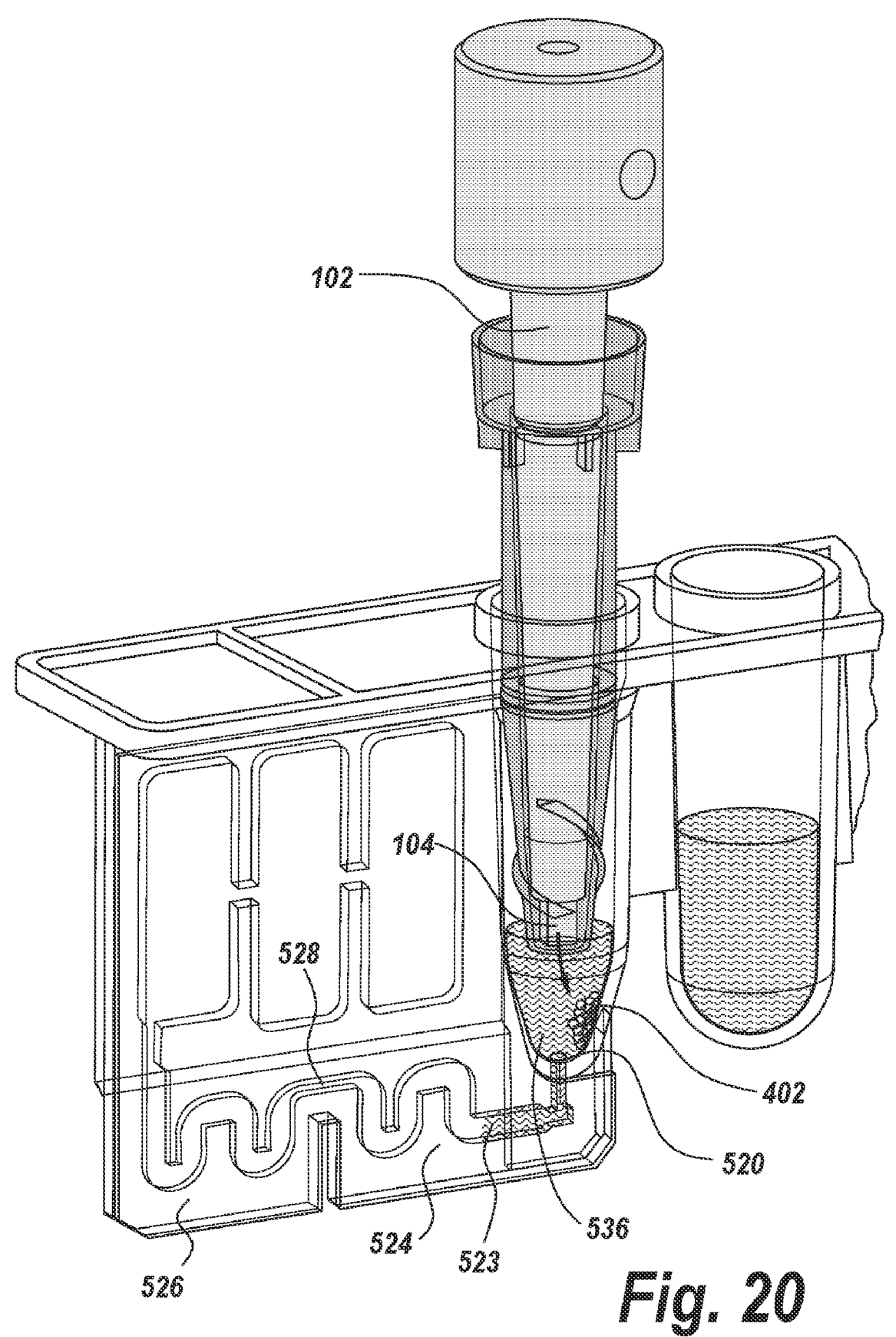
FIG. 20 illustrates the magnetic beads clustering on the side wall of the elution well, thereby clearing space between the rotor mixer tip and an aperture at the bottom of the elution well.
Figure 21:
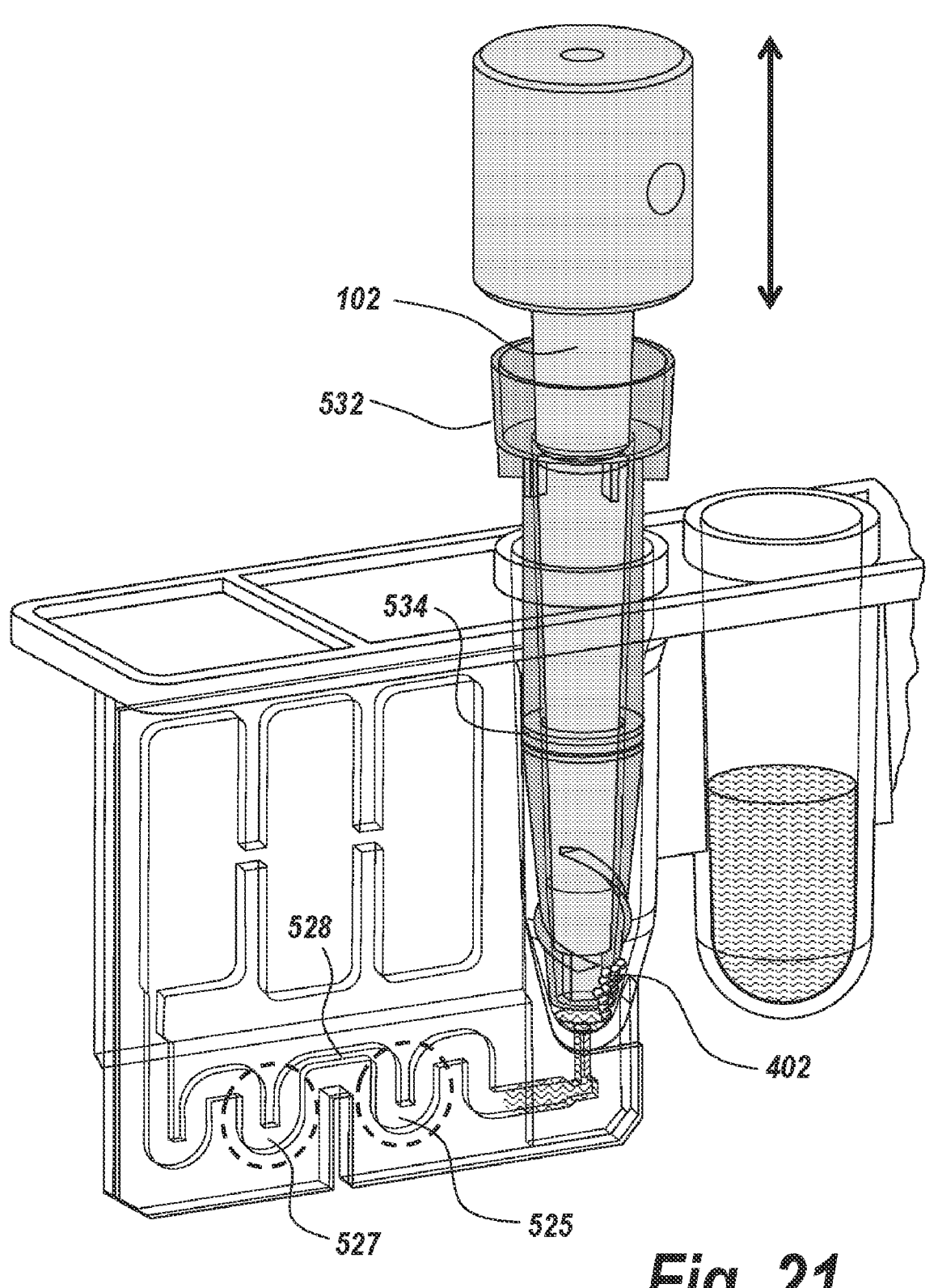
FIG. 21 illustrates pumping action exerted by vertical motion of a disposable sleeve fitted with an O-ring seal.
Figure 22:
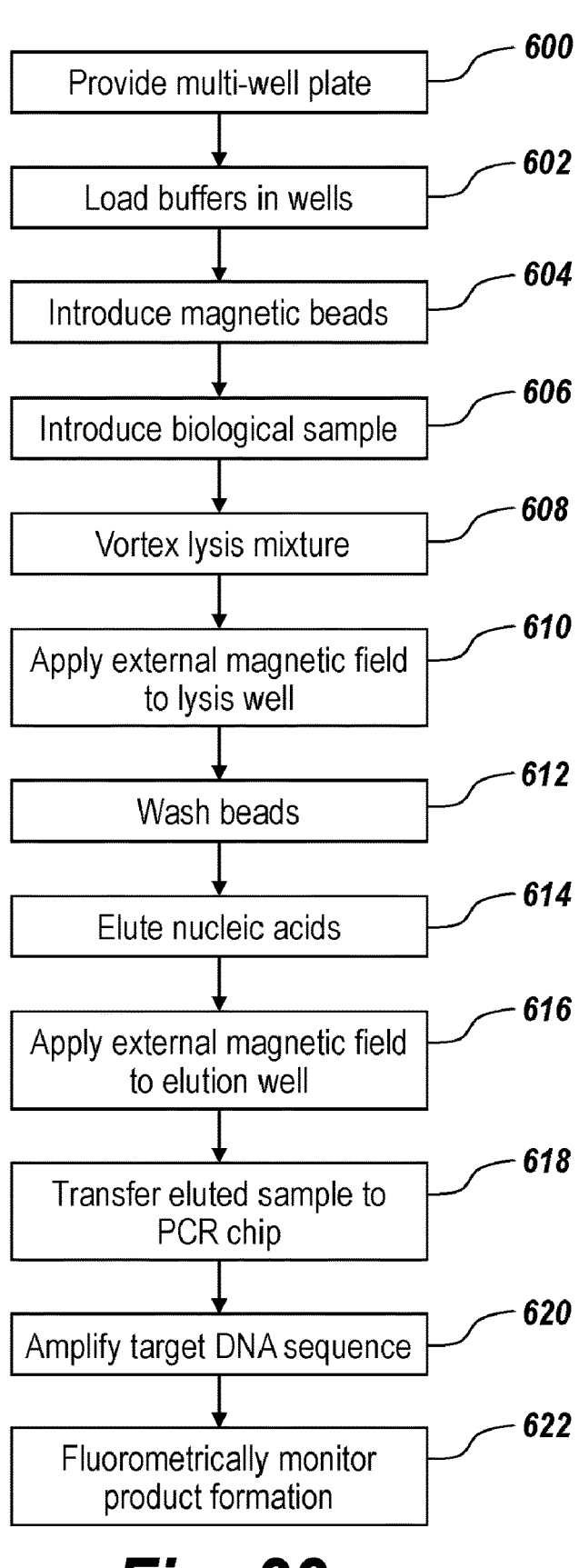
FIG. 22 is a flowchart of a method of nucleic acid sample lysis, purification, elution, PCR amplification, and fluorometric monitoring.

FIG. 18 illustrates step 616 where external magnet 116 being applied to the side wall of elution well 516, whereby magnetic beads 402 cluster against the side wall (FIG. 19). As seen in FIG. 20, this clustering of the beads clears the space between rotor tip 104 and aperture 520. By setting sleeve 532 in reciprocating motion along the vertical axis of elution well 516, pumping action is exerted on the eluted sample 536 (FIG. 21), whereby the eluted sample flows through aperture 520 and travels along channel 522 and into the PCR chip (step 618) where it combines with dry mixture 523 to form a PCR solution that collects in in first heat zone 524 and second heat zone 526. The O-ring seal 534 seals the interior of the elution well, whereby downward movement of the sleeve 532 increases the pressure within the elution well, below the seal, thus forcing the eluted sample into the PCR chip. Upward movement of the sleeve thus tends to decrease the pressure within the elution well, below the seal, advancing the sample in the opposite direction within the PCR chip.

Also, as anticipated above, the apparatus 100 is fitted with one or more PCR heating blocks (not shown) configured to heat one or more heat zones of the PCR chip such that the PCR solution undergoes denaturation in the first heat zone 524, annealing in the second heat zone 526, and extension in channel 528 therebetween. Further pumping action by sleeve 532 redistributes the contents of the PCR solution among different sections of the PCR chip, thereby subjecting its contents to a sufficient number of PCR cycles for amplifying DNA target sequences from the biological sample (step 620).

The amplification of a target DNA may be monitored in real-time during the PCR, either quantitatively or semi-quantitatively, by a laboratory technique also known as quantitative PCR ("qPCR"). Two common methods for the detection of PCR products in qPCR are (1) non-specific fluorescent dyes that intercalate with any double-stranded DNA and (2) sequence-specific DNA probes consisting of oligonucleotides that are labeled with a fluorescent reporter, which enable detection after hybridization of the probe with its complementary sequence. In both instances, the PCR chip may include one or more portions that are transparent in the absorbance and emission ranges of fluorescent reporter dyes so as to enable real time fluorometric monitoring of the PCR (step 622). In the exemplary embodiment of FIG. 21, fluorometric emission may be quantified by collecting light emitted by a reporter dye in first bend area 525 and/or second bend area 527 by means of a fluorometer (not shown).

The foregoing description has been directed to particular embodiments. However, other variations and modifications may be made to the described embodiments, with the attainment of some or all their advantages. It will be further appreciated by those of ordinary skill in the art that modifications to the above-described systems and methods may be made without departing from the concepts disclosed herein. Accordingly, the invention should not be viewed as limited by the disclosed embodiments. Furthermore, various features of the described embodiments may be used without the corresponding use of other features. Thus, this description should be read as merely illustrative of various principles, and not in limitation of the invention.

Many changes in the details, materials, and arrangement of parts and steps, herein described and illustrated, can be made by those skilled in the art in light of teachings contained hereinabove. It will be understood that certain features and sub-combinations are of utility and may be employed without reference to other features and sub combinations and are contemplated within the scope of the claims. Accordingly, it will be understood that the following claims are not to be limited to the embodiments disclosed herein and can include practices other than those specifically described, and are to be interpreted as broadly as allowed under the law. Additionally, not all steps listed in the various figures need be carried out in the specific order described.

We claim:

1. A sample lysis, nucleic acid extraction and amplification apparatus, comprising:
(i) a base for retaining a multi-well plate, the multi-well plate comprising: a lysis well, at least one wash well, and an elution well;
(ii) a vertically aligned rotor mixer comprising a rotor shaft having a magnetic tip disposed at an end thereof, said rotor shaft being driven by a rotor engine for creating a vortex in mixture including a biological sample when said rotor motor is inserted in one of the lysis well, the at least one wash well and the elution well;
(iii) a rotor mixer vertical actuator configured to impart elevational movement of the rotor mixer to selectively insert or remove the rotor mixer magnetic tip from a well of the multi-well plate,
(iv) a rotor mixer horizontal actuator configured to selectively impart horizontal movement of the rotor mixer between any two wells of the multi-well plate, and
(v) a PCR heating block configured to heat one or more heat zones in a PCR chip.

2. The apparatus of claim 1, wherein the base comprises a plurality of slots wherein each slot is configured to receive and engage with a well of a multi-well plate.

3. The apparatus of claim 1, further comprising a lysis well heating block configured to heat the lysis well of the multi-well plate.

4. The apparatus of claim 1, further comprising an elution well heating block configured to heat the elution well of the multi-well plate.

5. The apparatus of claim 1, wherein the rotor mixer magnetic tip is covered with a disposable protective sleeve comprising an O-ring seal.

6. The apparatus of claim 1, further comprising a fluorometer.

7. A system for isolating and amplifying nucleic acids from a biological sample, comprising the apparatus of claim 1 and a multi-well plate comprising: a lysis well, at least one wash well, an elution well, and a PCR chip.

* * * * *